(12) United States Patent
Morris (10) Patent No.: US 9,314,003 B2
(45) Date of Patent: Apr. 19, 2016

(54) MALODOR NEUTRALIZERS IN BIODEGRADABLE SUBSTRATES

(75) Inventor: Kathy Morris, Blacksburg, VA (US)

(73) Assignee: Kathy Morris, Scotch Plains, NJ (US)

( * ) Notice: Subject to any disclaimer, the term of this patent is extended or adjusted under 35 U.S.C. 154(b) by 536 days.

(21) Appl. No.: 13/343,070

(22) Filed: Jan. 4, 2012

(65) Prior Publication Data

US 2012/0167836 A1 Jul. 5, 2012

Related U.S. Application Data

(60) Provisional application No. 61/429,678, filed on Jan. 4, 2011.

(51) Int. Cl.
*A01K 13/00* (2006.01)
*A01K 27/00* (2006.01)
*A61L 9/01* (2006.01)

(52) U.S. Cl.
CPC .............. *A01K 27/007* (2013.01); *A01K 27/006* (2013.01); *A61L 9/01* (2013.01)

(58) Field of Classification Search
CPC .................................................... A01K 27/007
USPC .......................................................... 119/860
See application file for complete search history.

(56) References Cited

U.S. PATENT DOCUMENTS

| | | | | |
|---|---|---|---|---|
| 4,089,800 A | * | 5/1978 | Temple ................... | A01N 25/28 106/312 |
| 4,411,855 A | | 10/1983 | Fiebig, Jr. et al. | |
| 4,926,784 A | * | 5/1990 | Brightful ................ | A01K 13/00 119/653 |
| 5,373,815 A | * | 12/1994 | Sagebiel ................ | A01K 27/007 119/654 |
| 6,234,118 B1 | * | 5/2001 | Lahens .................. | A01K 27/007 119/654 |
| 7,741,266 B2 | | 6/2010 | Bell et al. | |
| 2003/0199421 A1 | * | 10/2003 | Copfer .................. | A01K 13/003 512/1 |
| 2005/0089540 A1 | * | 4/2005 | Uchiyama ............... | A61L 9/012 424/401 |
| 2009/0250371 A1 | | 10/2009 | Nicoll | |
| 2011/0293539 A1 | * | 12/2011 | Ibrahim ................ | A61K 8/0208 424/49 |
| 2012/0093901 A1 | * | 4/2012 | Loyen ............................ | 424/401 |

* cited by examiner

*Primary Examiner* — Kristen C Hayes
(74) *Attorney, Agent, or Firm* — New River Valley IP Law, P.C.; Michele L. Mayberry (57) ABSTRACT

The present invention relates to the field of deodorizers. More particularly, embodiments of the invention include plasticized cellulosic materials impregnated with zinc ricinoleate and in the form of replaceable hang tags and/or deodorizer inserts useful for suppressing, treating, or preventing offensive and/or undesirable odors. Particular embodiments of the invention include a solid plastic biodegradable deodorizer composition comprising: a cellulose acetate based substrate having at least 96% biodegradability; and a malodor neutralizer capable of forming a complex with one or more nitrogen- or sulfur-containing compounds and chosen from zinc ricinoleate, zinc chloride, zinc gluconate, zinc lactate, zinc maleate, zinc salicylate, zinc sulfate, and mixtures thereof, which is impregnated into the substrate up to approximately 20% of the weight of the substrate. A common object of embodiments is to treat, reduce, or eliminate offensive odors and more specifically can include deodorant and odor controlling devices to reduce or eliminate unwanted pet odors.

6 Claims, 12 Drawing Sheets

MALODOR NEUTRALIZERS IN BIODEGRADABLE SUBSTRATES

CROSS-REFERENCE TO RELATED APPLICATIONS

The present application relies on and claims priority to and the benefit of the filing date of U.S. Provisional Patent Application No. 61/429,678, filed Jan. 4, 2011, the entire disclosure of which is hereby incorporated herein by reference.

BACKGROUND OF THE INVENTION

Field of the Invention

The present invention relates to the field of deodorizers. More particularly, embodiments of the invention include plasticized cellulosic materials impregnated with zinc ricinoleate and in the form of replaceable hang tags and/or deodorizer inserts useful for suppressing, treating, or preventing offensive and/or undesirable odors.

Various products exist for removing and/or masking unwanted odors associated with animals, especially pets, and people. Known deodorizing techniques include static deodorants, aerosol sprays, powders, liquids, candles, and treated filters.

Static deodorants release fragrances or other substances into the environment to mask, cover, or counteract unwanted odors. Such deodorizers are limited by the ability of the deodorizing ingredients to diffuse throughout the target space. As such, as the area of the volume of space to be deodorized increases, the efficiency of static-type deodorizers decreases. Furthermore, if such products are used in smaller spaces, such as closets and gym bags, the product is effective while the space is closed but ineffective once the closet or bag is opened in a larger environment, such as a room, where the fragrance will immediately disperse and become less concentrated in the vicinity of the odor, e.g., shoes remaining in an open gym bag. Additionally, fragrances typically counteract odors but are chemically incapable of absorbing, destroying, or neutralizing the unpleasant odors sought to be eliminated.

A specific type of static deodorizer that has been proposed can be found in US Patent Application Publication No. 2003/0199421, the disclosure of which is hereby incorporated by reference herein in its entirety. This publication provides a polyethylene or polypropylene material impregnated with about 25% or more by weight of a fragrance, which is preferably configured in the form of a dog tag to be worn by a pet on its collar to provide a scent in the vicinity of the pet during use. Such products may be offensive to pets by containing such large amounts of perfumes and only serve to mask unwanted pet odors rather than eliminate or prevent the odors in the first place with a neutralizing agent. Furthermore, polyethylene and polypropylene substrates are typically not biodegradable.

Other static deodorizers capable of absorbing odors in limited volumes have been used, including boxes of baking soda or activated charcoal type products. For these types of products to be effective for the absorption of odors, rapid air circulation throughout the volume of space being treated is typically required. Such products are also inconvenient, can be messy when replacing the deodorizer, or can be spilled during use due to the particular form in which they are packaged, i.e., powders. Accordingly, such deodorizers are inappropriate for certain applications, including for the deodorizing of pets, purses, gym bags, and luggage to name a few, which are susceptible to movement.

Particular applications for odor control have also been presented in the context of controlling odors associated with animal waste. For example, attempts have been made to control the odor associated with animal fecal material, including for example formulations disclosed in US Patent Application Publication No. 2006/0228323, the disclosure of which is hereby incorporated by reference herein in its entirety. The formulation contains an amphoteric surfactant for removing malodors from animal waste. Specifically, the formulation, when sprayed or fogged, forms a chemical complex with the odorous gas molecules thereby eliminating the unwanted odors. The formulation may be used to treat solid waste but only to the extent that the solid waste contains gas or liquid phase within it.

Filters have also been used to deodorize air or reduce air pollution levels in environments in which animals are kept or in human living spaces. Filters are usually treated with deodorizing compositions such as activated charcoal or baking soda, but such compositions have limited efficacy unless used in combination with circulating fans to move the air being treated through or otherwise in contact with the deodorizing composition. Further, filters are effective deodorizers when located in close proximity to the source of the malodor. Thus, the efficacy of these products is usually limited to uses such as kitchen fans.

Powdered-type carpet and shoe deodorizers also exist for treating rooms affected by pet odors, or even shoes. Such products can contain fragrances and/or absorbents such as baking soda, and again their efficacy depends on diffusion of the active deodorizing agent into the area being treated. Thus, it has been found that powdered carpet or shoe deodorizers are effective in masking or absorbing odors present in carpets or shoes to which they are applied, but are less effective in eliminating odors already present in the air surrounding such objects.

Deodorizers can also be dispensed into the air in the form of aerosols or sprays, i.e., sprays of gaseous suspensions of or liquid droplets of the deodorizers. The use of aerosols permits more effective deodorization because the particles or droplets containing the deodorizing ingredients may be distributed throughout the room, may be applied to fabric surfaces such as carpets, shoes, clothing, and furniture, or may be dispersed throughout other volumes to be deodorized. The application of aerosol sprays is not dependent upon the relatively slow molecular diffusion required by static or similar deodorizers. However, currently available aerosol sprays are subject to other serious disadvantages. For example, most such products contain only fragrances which, as noted above, do not absorb, neutralize or destroy malodors but merely mask them by adding a more pleasant odor for a limited time. Aerosols can also contain unwanted environmentally-destructive compounds such as CFCs. Furthermore, pets and humans sensitive to perfumes may find aerosols dispersed into the atmosphere annoying, offensive, or detrimental to their health, e.g., in the case of asthmatics.

Certain aerosol sprays are dispensed in the form of relatively large liquid droplets which dissolve odorant molecules from the atmosphere before dropping out of and thereby cleansing the air. This mechanism is at best a temporary remedy since after removal of the droplets from the atmosphere the malodors can be re-released. Moreover, many malodorous compounds are insoluble in the droplets and consequently cannot be removed from the air in this manner.

Oxidizing agents have also been used as room deodorizers. Known oxidizing-type deodorizers include those having less than about 1% of an oxidizing agent, such as sodium chlorite. Sodium chlorite based products, however, are only effective against readily oxidizable malodors. Moreover, the prolonged use of such an oxidizing agent, or the use of higher concentrations of oxidizing agents, may pose a potential safety hazard. This type of product thus has limited safety and efficacy.

Numerous types of aerosol disinfectant sprays are also known, and marketed, for use as room deodorizers. Such disinfectant sprays may contain anti-microbial agents intended to kill odor causing bacteria. Significantly, however, many odors are not the result of bacterial action. Moreover, disinfectant aerosols do not eliminate malodors already present in the atmosphere. In light of the disadvantages presented by existing techniques for reducing the effect of offensive malodors emanating from various sources, improved deodorizer compositions, deodorizer vehicles, and deodorizing methods are highly desired.

SUMMARY OF THE INVENTION

As will be discussed in detail below, the present invention provides numerous embodiments of improved deodorizing products and methods, which are effective for treating, eliminating, or preventing undesirable or offensive malodors capable of being perceived by humans or animals, and which are usually associated with pets and/or human body odors.

It is noted that these and other aspects of the present invention will be more apparent from the following description. The features and advantages of the present invention will be apparent to those skilled in the art. While numerous changes may be made by those skilled in the art, such changes are within the spirit of the invention. Additionally, some embodiments of the present invention will be discussed relative to various figures provided. These drawings and graphics illustrate certain aspects of some of the embodiments of the present invention, and should not be used to limit or define the invention.

It is believed that malodors, eg, odors which are offensive to the human or animal sense of smell, are caused by a number of compounds. These chemical compounds having offensive smells include, to name a few, aliphatic halohydrins, aliphatic amines, aliphatic N-oxides, dialkylamines, cycloaliphatic amines, cycloaliphatic N-oxides, cyclo-olefinic amines, cyclo-olefinic N-oxides, cycloaromatic amines, cycloaromatic N-oxides, hydroxyalkylamines, imine compounds, amide compounds, amino acids, polypeptides, modified antimicrobial proteins, diureides, nitriles, aliphatic mercaptans, cycloaliphatic mercaptans, mercaptoalkanoic acids, mercaptoalkanoic acid esters, aliphatic monosulfides, disulfides, trisulfides, sulfur oxides, sulfones and sultones, cycloaliphatic monosulfides, disulfides, trisulfides, sulfur oxides, sulfones and sultones, cyclo-olefinic monosulfides, disulfides, trisulfides, sulfur oxides, sulfones and sultones, cycloaromatic monosulfides, disulfides, trisulfides, sulfur oxides, sulfones and sultones, alkali metal sulfites, bisulfites and metabisulfites, isothiocyanates, thiocyanates, dithiocyanates, isothiazolones, isothiazolinones, thiodiazinethiones, halosulfamates, aryl sulfonamides, lower aliphatic carboxylic acids, phenols, phosphines, aliphatic phosphites and phosphonates, cycloaliphatic phosphites and phosphonates, arsines, lower alcohols, lower ketones, hops, hops acids, aryl pyrazoles, oxazolines, isocyanurates, biguanides, extracts of krameria, hydantoins, pyrollidones, pyrollidone carboxylic acids, pyrollidone carboxylic acid esters, nitrophenols, N-substituted aspartic acids and pyrethroids. Chemical compounds of these classes, which tend to have unpleasant, unwanted, or undesirable odors are referred to in this application as malodor compounds or malodors.

Others have attempted to combat such malodors with various deodorizer compositions. One such class of compositions employs cyclodextrins for reducing odor. It has been noted, however, that cyclodextrins tend not to perform well in certain environments, such as water-rich environments like laundry. Even further, the mechanism by which cyclodextrins work tends to mask the unwanted odors rather than neutralize or inactivate the odors.

In contrast, embodiments of the present invention include malodor neutralizing compounds such as zinc ricinoleate or other equivalent compounds which work by chemically reacting with nitrogen- and sulfur-containing compounds, frequent sources of bad odor. Another advantage of this type of deodorizing compound is that it will not interfere with most fragrances because fragrances do not usually contain sulfur or nitrogen. Thus, embodiments of the invention can also include fragrances for further deodorizing effects.

It has been reported that the investigation of zinc ricinoleate by means of molecular dynamics calculations reveals a very peculiar behavior of this material which looks very simple on first view. Compared to other odor absorbers which work by covering (like fragrances), disinfection or loose physical addition as starch derivatives, zinc ricinoleate is a complex metallorganic system which is especially efficient in absorbing nucleophil compounds. As most of the malodors are in fact good nucleophiles as amines or thioderivatives, it is an excellent base for high performance odor absorbing products in household, commercial, or industrial applications. Most fragrances are based on aliphatic or aldehydic terpene systems which do not interact with zinc ricinoleate as they are not sufficiently nucleophil. Using zinc ricinoleate, a successful odor absorbing can be achieved without interfering with the fragrance system.

The mechanism by which the active deodorizing agents of the present invention work is believed to include at least one or more of the following: chemically reacting with malodor molecules, complexing with malodor molecules, absorbing malodor molecules, encapsulating malodor molecules, and/or influencing the ability of human sensory receptors to perceive malodors (e.g., anosmia). For example, active malodor neutralizing agents suitable for use in accordance with exemplary embodiments of the invention may combat malodors by chemically reacting or complexing with malodor molecules, by blocking human sensory reception sites that detect the presence of malodor, or by otherwise treating, blending, reacting, or counteracting malodors without increasing the perceived overall odor level in a particular environment. In accordance with one aspect of an exemplary embodiment of the invention, metallic salts can be used effectively as the active malodor neutralizing agents.

For example, malodor neutralizing agents may comprise a metallic salt, preferably a water-soluble zinc salt. Zinc ricinoleate controls malodors selectively through a chemical binding of low molecular weight organic compounds containing the osmogene functional groups. On the other hand, zinc ricinoleate generally has no effect on carbonylic groups, such as aldehydes and ketones, which comprise typical perfume and fragrance components. Beneficially, zinc ricinoleate may stably complex with malodor molecules. The mode by which zinc ricinoleate complexes with malodors is similar to and can be compared to the iron binding and transport of oxygen in hemoglobin—the zinc acts as a catalyst to bind the malodor molecules, complexing it with the fatty acid side chains of the zinc ricinoleate molecule. In this way, the zinc ricinoleate neutralizes the malodors—that is, it reduces the level of undesirable malodors available for human perception. Preferably, in accordance with the present invention, zinc ricinoleate molecules complex with one or more malodor molecules, depending on the size and shape of the malodor molecule(s). Once the complex is formed, it is a stable complex, that is, the malodor molecule will not be released from the zinc ricinoleate.

Preferably, the metallic salt is at least one of zinc ricinoleate, zinc chloride, zinc gluconate, zinc lactate, zinc maleate, zinc salicylate, zinc sulfate, and mixtures thereof. Most preferably, the metallic salt is zinc ricinoleate, shown as Formula I below:

Formula I

Zinc Ricinoleate
9-Octadecenoic acid, 12-hydroxy-, zinc salt (2:1), (9Z,12R)-
CAS NO.: 13040-19-2
Molecular Formula: $C_{36}H_{66}O_6Zn$
Molecular Weight: 660.314640 [g/mol]

In order for compositions such as zinc ricinoleate to form bonds with malodor molecules, the zinc atoms should be activated so as to expose their action sites. The activation of zinc ricinoleate is typically achieved by solubilizing the compound prior to inclusion of the compound in the substrate material. Some malodor neutralizing materials, such as pure zinc ricinoleate, are waxy solids and the solubilization of zinc ricinoleate may not be an easy task. By using TEGO SORB 50, for example, the zinc compound is already in solubilized form and the reaction sites of the zinc compound is available to form bonds with nitrogen and sulfur atoms of target malodors.

In embodiments, the active malodor neutralizing agent is zinc ricinoleate, for example such as that commercially available under the trade name TegoSorb from Evonik Goldschmidt Corporation in Hopewell, Va., USA. This compound is available in formulations containing the zinc salt of a fatty acid in combination with various solubilizers. A preferred formulation is the TEGO SORB CONC. 50, Product Code 201758 (50% active, liquid, water dispersible). Other compositions can be used to introduce the active deodorizing component to the cellulosic material, including for example, TEGO Sorb PY 88 TQ (100% active, waxy solid, water insoluble); TEGO Sorb A 30 (30% active, liquid, water soluble with Baypure, low toxicity, biodegradable, powdery residue); TEGO Sorb Ready 30 (30% active, liquid, water soluble with citric acid), also manufactured by Evonik. The components of TEGO SORB 50 are shown below in Table 1:

TABLE 1

| TEGO SORB 50 | | |
|---|---|---|
| Component | CAS No. | Concentration |
| 1,2,3-Propanetricarboxylic acid, 2-hydroxy | 77-92-9 | <0.003% |
| Phenol, 2,6-bis(1,1-dimethylethyl)-4-methyl- | 128-37-0 | <0.01% |
| 1,2-propanediol | 57-55-6 | 5% |
| Alcohols, C12-14, ethoxylated | 68439-50-9 | 30% |
| 9-Octadecenoic acid, 12-hydroxy-, zinc salt (2:1), (9Z,12R) | 13040-19-2 | 49.94% |

In embodiments, the preferred delivery vehicle for delivering the malodor neutralizer is a biodegradable substrate. In embodiments of the invention, it is preferred that the substrate, and/or the substrate impregnated with the malodor neutralizer and optionally the fragrance, be biodegradable or at least about 95% biodegradable or higher, such as 96%, 97%, 98%, 99%, approaching 100%, or 100% biodegradable.

For example, a process for preparing scented cellulosics can be used as described in U.S. Pat. No. 7,741,266 and US Published Patent Application No. 20100319576 of Rotuba Extruders, Inc. of Linden, N.J., the disclosures of which are hereby incorporated by reference herein their entireties. The active malodor neutralizing agent can be added to the manufacturing process with the fragrance or in place of the fragrance in amounts needed to achieve a desired effect and intensity of fragrance as well as longevity of the malodor neutralizer in the final product. The term "cellulosic" refers to cellulose acetates and cellulose acetate esters and includes, but is not limited to, cellulose acetate, cellulose acetate propionate, and cellulose acetate butyrate. Cellulose acetate esters include, but are not limited to, cellulose diacetate and cellulose triacetates. The term "cellulosic" also includes all hydrates of cellulosics (e.g. anhydrous cellulose acetate, cellulose acetate monohydrate, cellulose acetate dihydrate, cellulose acetate trihydrate, and cellulose acetate tetrahydrate) as well as anhydrous forms of cellulosics. Typically, the methods of manufacturing the deodorizer compositions according to the invention may include combining an amount of zinc ricinoleate with cellulose acetate and a plasticizer, optionally with a fragrance. The composition is allowed to cure for a time and under conditions sufficient to achieve a desired final product. For example, any desired hardness of the final product can be achieved by modifying the amount of plasticizer added. For hard melt type compositions, the plasticizer can be added in the range of about 10% to about 30% based on weight of the components in the composition. For a soft melt composition, more plasticizer can be added, for example from about 30% to about 50% based on weight of the composition. A solvent is also desired to achieve having the zinc ricinoleate in an active form.

Preferably, in embodiments of the invention, zinc ricinoleate is used at a level of about 0.01% to about 5.0% by weight of the components making up the final product, preferably at a level of about 0.2% to about 3.0%. Other concentrations, including up to about 10% or even 20% by weight of the components in the final products or the weight of the final product itself, are feasible. Such high concentrations may be desired to create a product with a longer life of activity, however, for the applications described in this specification, concentrations below about 2% by weight should suffice. One such malodor eliminator is the Malodor Neutralizer Absorbzio Sz 42011 (Sozio Inc. of Edison, N.J., USA), which is a mixture of zinc ricinoleate, with various solvents, and fragrance, which is well known for its anti malodor properties against amine type odors and some aromachemicals. Absorbzio is a highly effective deodorant/malodor absorber based on the zinc salt of ricinoleic acid (present in nature in the form of triglycerides in the seeds of various plants such as the castor oil plant) associated with fresh and long lasting aromatic compounds. Absorbzio effectively eliminates malodors derived from ammonia, mercaptan, sulfur, smoke, fish, onion, and garlic through chemical binding. Once a bad odor is absorbed using Absorbzio, it will not be released, as a permanent binding of the odor takes place. Further, Absorbzio is plant derived, non-toxic, and readily biodegradable.

The IFRA Certificate for Absorbzio provides that concentrations in a substrate are acceptable up to about 20%. Thus, the plastic substrate embodiments of the invention could be formulated to comprise up to 20% by weight of the components used to form the final product, or by weight of the final products themselves. Embodiments of the invention typically comprise less, such as about a 3% concentration in the plastic substrate (based on weight of the final product), for example in the case of a 30 mm×30 mm×3 mm tag there may be about 3% of Absorbzio in about 5 grams of plastic, or a total of 0.15 grams Absorbzio in the plastic substrate.

If desired, fragrances which have been formulated to meet US CPSC (Consumer Product Safety Commission) safety requirements for Toys can be incorporated into the plastic substrate as well. Indeed, any desired fragrance can be incorporated, however, preferred are materials that meet safety standards. For example, it may be desired to meet the safety requirements as per International Fragrance Association (IFRA) standards (such as IFRA Category 1). These types of fragrances are designed using FDA GRAS (Generally Regarded As Safe) ingredients.

Preferred embodiments of the invention incorporate a lemon fresh scent, a linen fresh scent, or are fragrance free, with just malodor. These fragrances have been found to be especially pleasing scents to combat pet and body odor.

The plastic substrate materials can be formed into any desirable shape using any means of manufacturing such as molding or casting. Preferred shapes include a long oval dog tag shape (rounded edges rectangular shape), which can be used as pet tags and/or replacement inserts for a variety of products, including gym bags and luggage.

BRIEF DESCRIPTION OF THE DRAWINGS

The accompanying drawings illustrate certain aspects of some of the embodiments of the present invention, and should not be used to limit the invention. Together with the written description the drawings serve to explain certain principles of the invention.

DETAILED DESCRIPTION OF VARIOUS EXEMPLARY EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Included in embodiments of the invention is a solid plastic biodegradable deodorizer composition comprising: a cellulose acetate based substrate having at least 96% biodegradability; and a malodor neutralizer capable of forming a complex with one or more nitrogen- or sulfur-containing compounds and chosen from zinc ricinoleate, zinc chloride, zinc gluconate, zinc lactate, zinc maleate, zinc salicylate, zinc sulfate, and mixtures thereof, which is impregnated into the substrate in an amount up to about 20% of the weight of the substrate.

Such deodorizer compositions can be in any form including that of a plurality of pellets or beads. For example, in deodorizer compositions according to the invention, the beads or pellets are contained in a plurality of sachets.

In embodiments, the deodorizer composition substrate is an elongated planar member capable of insertion into a breathable pocket on an interior of a bag. Such compositions can be used with bags including luggage, a purse, a lunch box, a briefcase or a backpack.

In further embodiments, the deodorizer compositions described in this specification can comprise a fragrance impregnated into the substrate, and especially preferred is a fragrance that does not contain nitrogen or sulfur.

The present invention also includes a malodor neutralizer dog tag comprising: a cellulose acetate based substrate having at least 96% biodegradability; a malodor neutralizer capable of forming a complex with one or more nitrogen- or sulfur-containing compounds and chosen from zinc ricinoleate, zinc chloride, zinc gluconate, zinc lactate, zinc maleate, zinc salicylate, zinc sulfate, and mixtures thereof, which is impregnated into the substrate in an amount up to about 20% of the weight of the substrate; a fragrance impregnated into the substrate that does not contain nitrogen or sulfur and is present in an amount effective to mask odors perceptible to humans but cause no adverse reaction from dogs.

Also included within the scope of the invention is a pet deodorizing system comprising: a collar operably configured for attaching to a pet's neck; and a plurality of cellulose acetate based substrates having at least 96% biodegradability and comprising impregnated therein zinc ricinoleate in an amount up to about 3% of the weight of the substrate and a nitrogen- and sulfur-free fragrance in an amount effective to mask odors perceptible to humans but cause no adverse reaction from a pet when disposed on the collar attached to the pet; wherein the collar and substrates are operably configured for releasable engagement with one another.

Deodorizing systems according to embodiments of the invention can comprise one or more substrates that is a pendant operably configured to hang from the collar when engaged therewith. Preferred are deodorizing systems wherein one or more of the substrates is an elongated strip and the collar is operably configured to allow for about 50% or more of one side surface of each strip to be exposed to air when engaged with the collar. Even further, the deodorizing systems can have one or more substrate that is an elongated strip comprising a through hole at each of opposing ends of the strip to allow for opposing ends of the collar to be received and secured therethrough with snaps.

Embodiments of the invention also include a deodorizing pendant comprising a cellulose acetate based substrate impregnated with zinc ricinoleate and optionally a fragrance, operably configured to magnify or distort an image viewed from an upper surface of the substrate which is disposed on a lower surface of the substrate.

Pendants according to the invention can comprise zinc ricinoleate present in an amount up to about 1.5% based on weight in the substrate.

The inventive deodorizing systems can comprise a plurality of the inventive pendants, if desired.

A method of manufacturing a plastic deodorizer is also included within the invention and can comprise: combining zinc ricinoleate, cellulose acetate, and a plasticizer in a solvent; allowing the composition to cure for a time and under conditions sufficient to provide a plastic deodorizer composition with a desired hardness. If desired, such methods can also comprise adding a fragrance to the deodorizer.

Figures 1A, 1B:
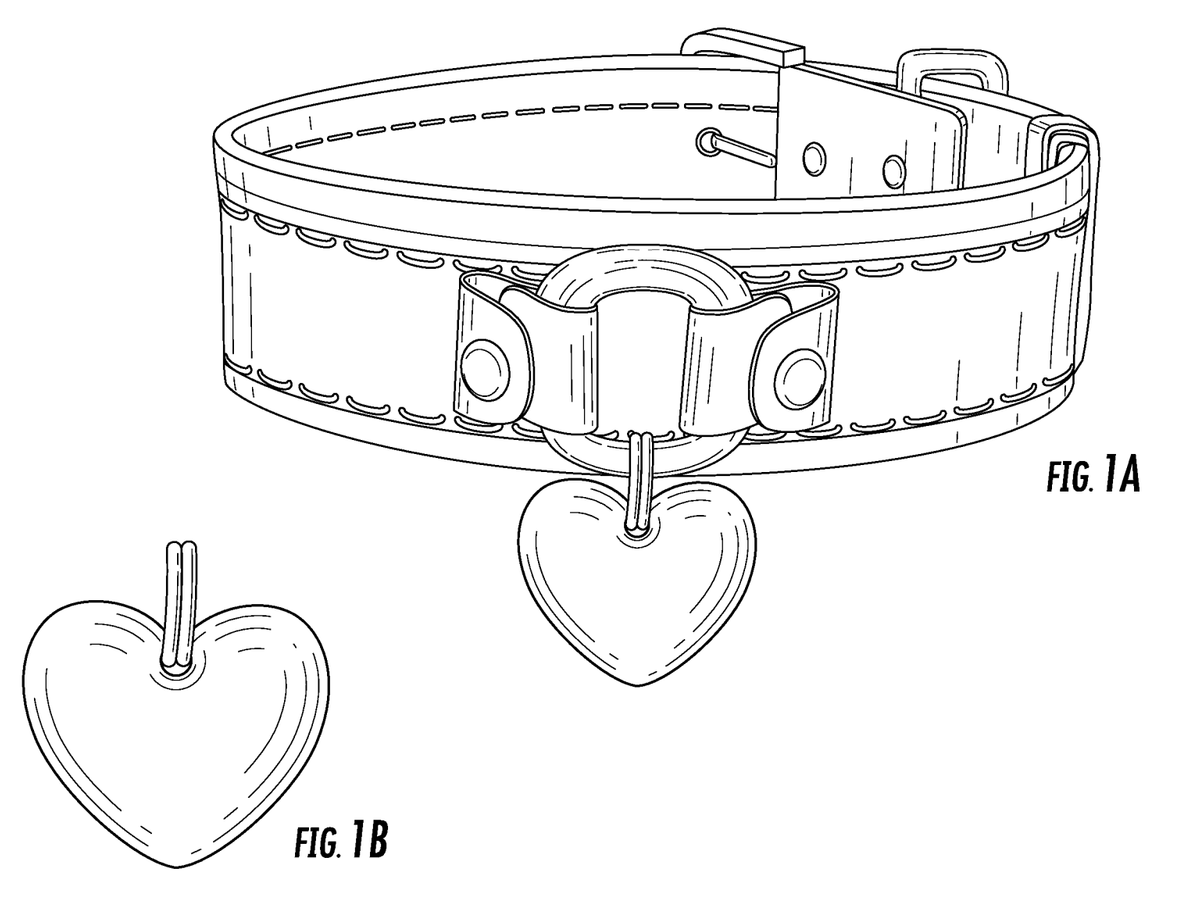
FIGS. 1A and 1B is a schematic diagram of an embodiment of a pet collar according to embodiments of the invention in which a malodor neutralizer pendant can be incorporated and replaced.

As shown in FIGS. 1A and 1B, embodiments of the invention include pet collars, such as dog collars, which are operably configured for receiving, retaining, and releasing one or more deodorizers of the present invention. More particularly, as shown in FIG. 1A, a cellulosic substrate comprising a malodor neutralizer and optionally a fragrance impregnated therein can be formed to be received and retained by a dog collar in a releasable manner. As shown, one mechanism for attachment can be provided by a ring capable of being retained by snap-held fastening means disposed on the collar. In this manner, replacement pendants attached to the ring can be interchanged in the dog collar, especially when the deodorizing composition and/or fragrance is beyond its effective period of use. In embodiments, the ring itself can comprise a cellulosic substrate with a malodor neutralizer and optional fragrance. Alternatively, the replacement pendants can be configured without an additional ring (FIG. 1B) for attachment to other structure disposed on the dog collar, such as a typical ring as shown.

Figures 2A, 2B:
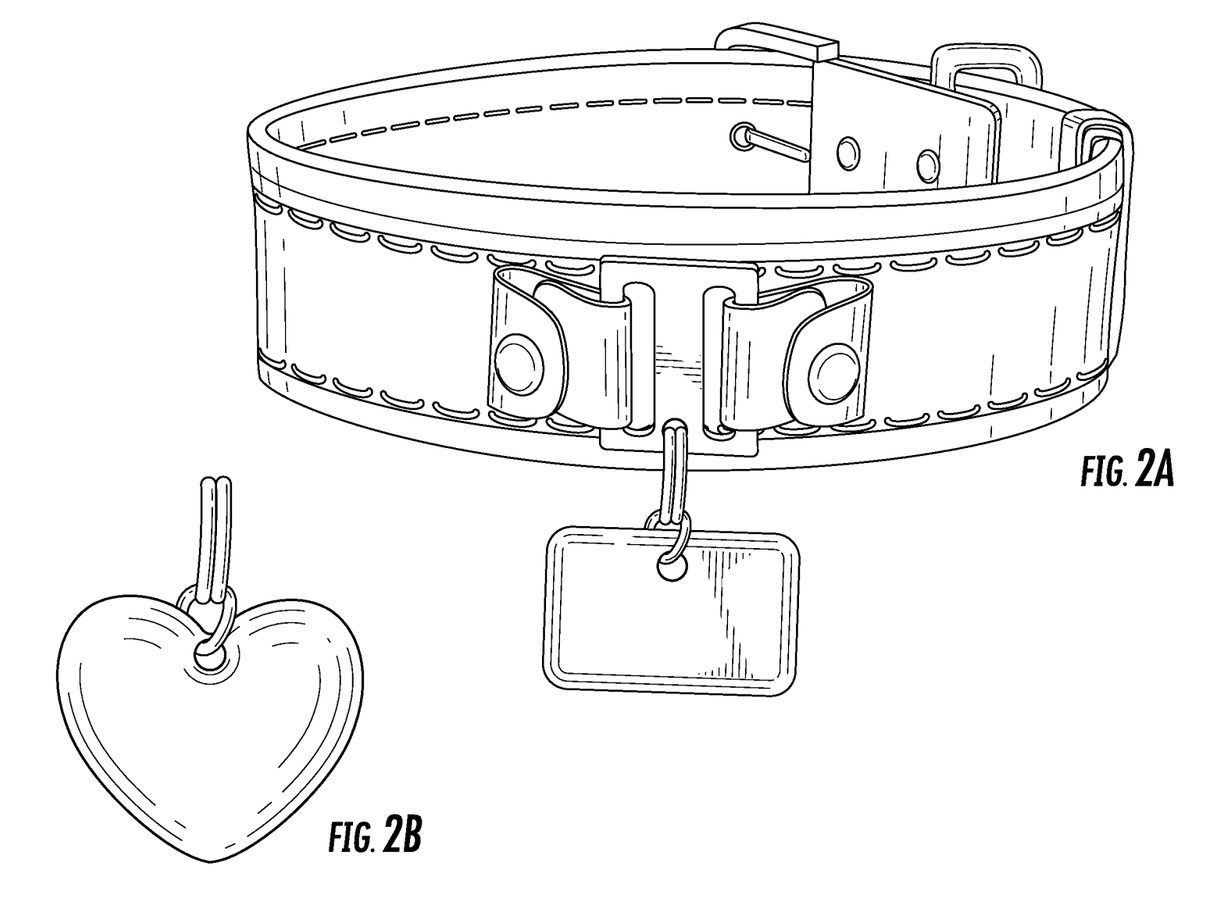
FIGS. 2A and 2B is a schematic diagram showing an alternative embodiment for a replaceable malodor neutralizer pendant for a dog collar.

FIGS. 2A and 2B provide additional embodiments for the replaceable deodorizers according to the invention. As shown in FIG. 2A, instead of a ring member, the means for attaching the pendant to the collar can be configured with additional material in the center of the ring member to provide additional support and/or additional surface area on the plastic substrate cellulosic material for the deodorizer and/or perfume to be dispersed into the atmosphere. Pendants (FIG. 2B) can then be interchanged for example by way of a ring directly on and off the support member or the entire support member can be replaced from the collar due to corresponding interacting structure (snaps) disposed on the collar. It is noted that although the pendants shown in FIGS. 1B and 2B are illustrated for use in connection with pet collars, such pendants would be equally applicable to other applications, including for use as a pendant on a necklace, belt, or bracelet for people. The plastic substrates are prepared in a manner that provides for an attractive pendant which functions as a scent neutralizer. It may be preferred that such pendants be used in place of deodorants or perfumes typically applied directly to the skin. Even further, such pendants, especially without colognes or perfumes, may be desirable for hunters who seek to minimize their human scent while hunting.

Figure 3:
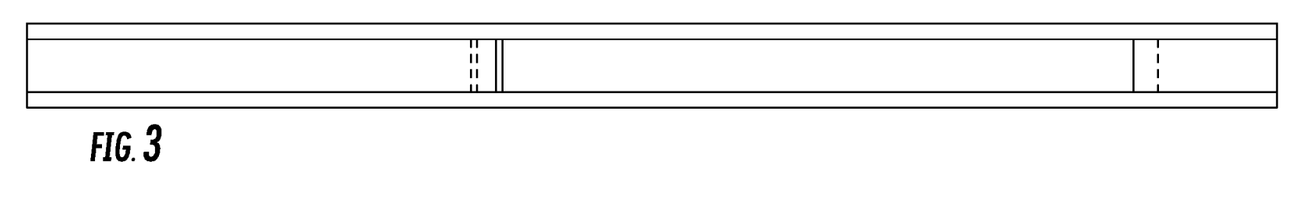
FIGS. 3, 4A, and 4B are schematic diagrams showing respectively a bottom planar view of an animal collar, with a replaceable malodor neutralizer strip, and a top planar view of the collar illustrating a means for securing the replaceable strip to the collar in a detachable manner that also exposes the strip to the environment.
Figure 4A:
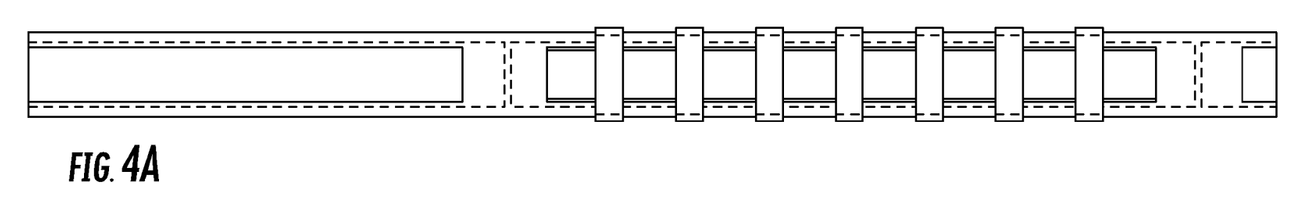
Figures 4B, 5A, 5B:
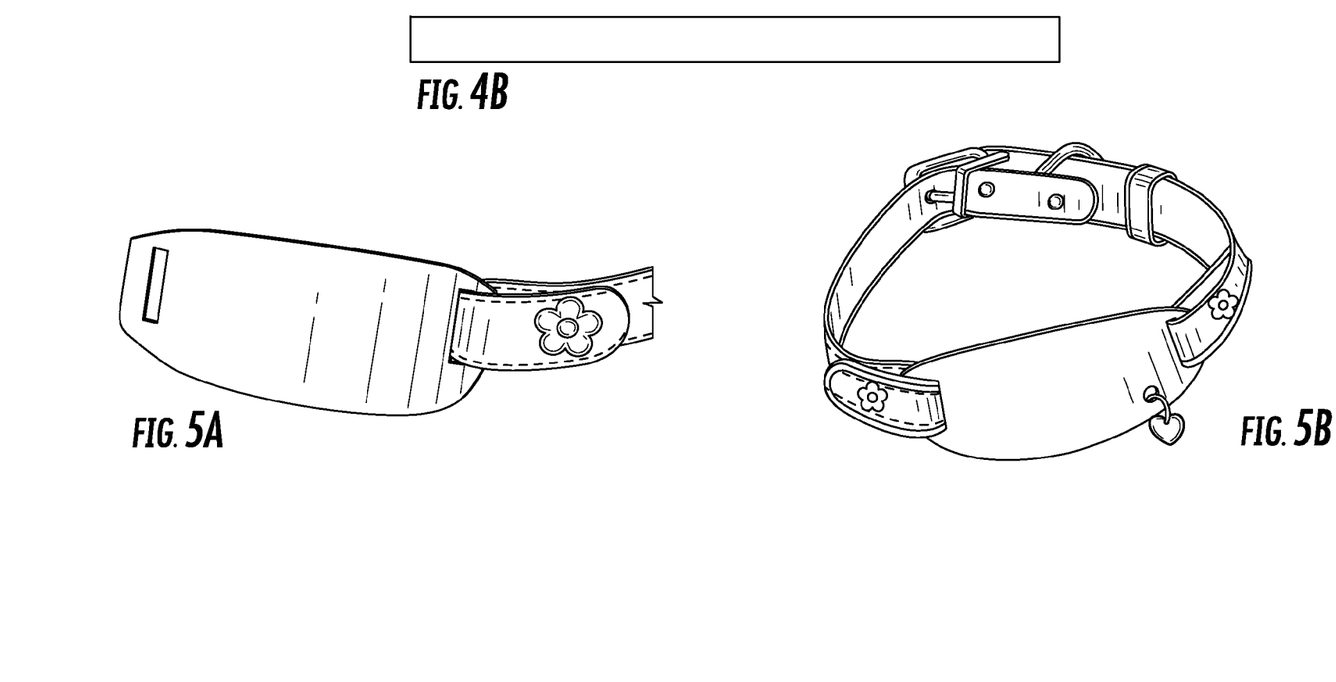
FIGS. 5A and 5B are schematic diagrams showing another embodiment of a pet collar according to the invention in which the malodor neutralizer is joined to the collar by the ends of the malodor neutralizer.

FIGS. 3, 4A, and 4B provide various views of another collar embodiment according to the invention. FIG. 3 is a bottom planar view of the collar (the side typically contacting the animal's neck). FIG. 4A is a top planar view of the collar showing a replaceable insert (FIG. 4B), which can be retained in or on the collar by way of any mechanism providing for releasable engagement with the collar. As shown, a preferred mechanism for attaching the insert to the collar is by way of multiple straps disposed along the length of the collar. In this manner, a substantial portion of the surface of the cellulosic material comprising the deodorizer composition and optionally a fragrance is exposed and available to interact with malodors. Other mechanisms for attaching the substrate of FIG. 4B to the collar can include using an adhesive, Velcro, or snaps, to name a few. It is preferred that at least about 30% of the entire surface area of the elongated strip be exposed to air when engaged with the collar. For example, about 50% of one side of the elongated strip can be exposed while the remainder is retained or facing the collar material. Any amount of substrate strip exposed to air will be effective, including from about 5% to about 95% of the surface area of the strip or the surface area of one or more sides of the strip.

In this embodiment, the cellulosic strip is flexible to allow for the collar to be shaped around an animal's neck. Even further, the cellulose acetate substrate strip can also be formulated to allow for only some amount of bending of the strip during use on the collar to provide for a more comfortable fit for the dog. In other embodiments, a series of cellulosic strips can be inserted into the collar. The series of strips, for example, 6-10 strips, need not be flexible as the number of strips aligned end to end along the length of the collar would allow for the collar to be flexible. More specifically, using several substrate strips that are not bendable will allow the collar to bend at portions not engaged with the strips.

Embodiments also include where the collar is operably configured to allow for a portion of the strip to be exposed to air and the strip repositioned to expose a different portion of the strip, such as turning the elongated strip over to expose the side of the strip previously facing the collar, or sliding the strip within the securing means of the collar to expose portions of the collar previously concealed, such as portions of the collar previously held to the collar by the several retaining straps along the length of the collar. The collar can also be configured to provide for exposure of the substrate strips on both side of the collar.

FIGS. 5A and 5B provide another embodiment for a collar or bracelet according to the invention. As shown, a replaceable insert comprising the cellulosic substrate material with deodorizing composition impregnated therein and optionally a fragrance can be configured for releasable engagement with the collar or other straps used as a bracelet. For example, in this embodiment, the surface area exposed to the air is maximized by configuring the replacement insert to be received by the collar using through holes disposed at both elongated ends of the insert. In this manner, both the top and bottom surfaces of the insert may come into contact with air for neutralizing any malodor compounds that may be present.

It is noted that the invention can be embodied in any form and for any particular application, and that the particular applications described in this specification are intended to serve as platforms and provide guidance in formulating products for similar applications. For example, the dog tags, pendants, and elongated strips of impregnated cellulosic material can also be modified for controlling or minimizing odors from pets contained in terrariums. More specifically, embodiments of the invention include using the impregnated substrates as terrarium accessories, in the form of rocks, leaves, or bark, to hold down amphibian odors.

Figure 6A:
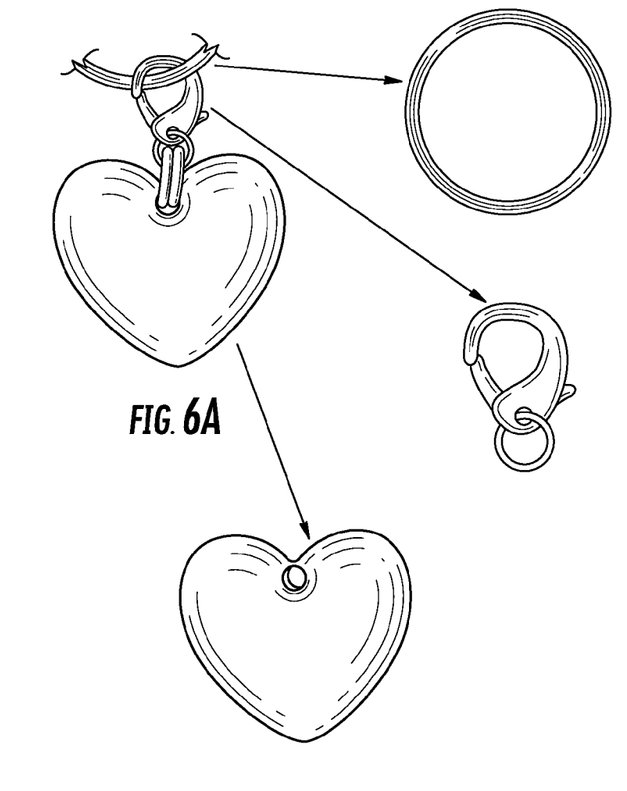
FIGS. 6A-C are schematic diagrams showing various malodor neutralizer pendants according to embodiments of the invention and means for securing the pendants to another article, such as a collar.
Figures 6B, 6C:
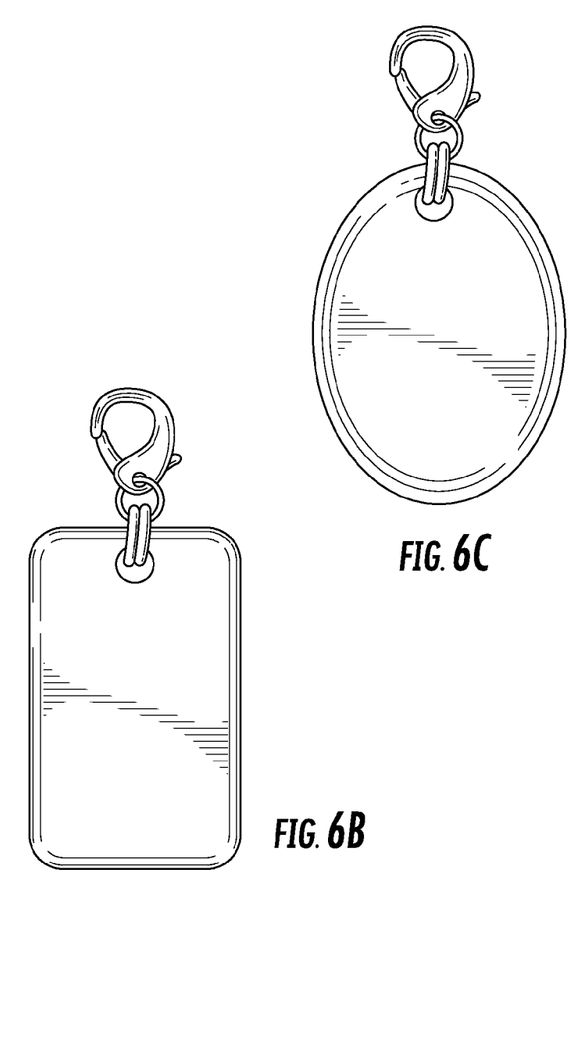
Figures 7A, 7B, 7C:
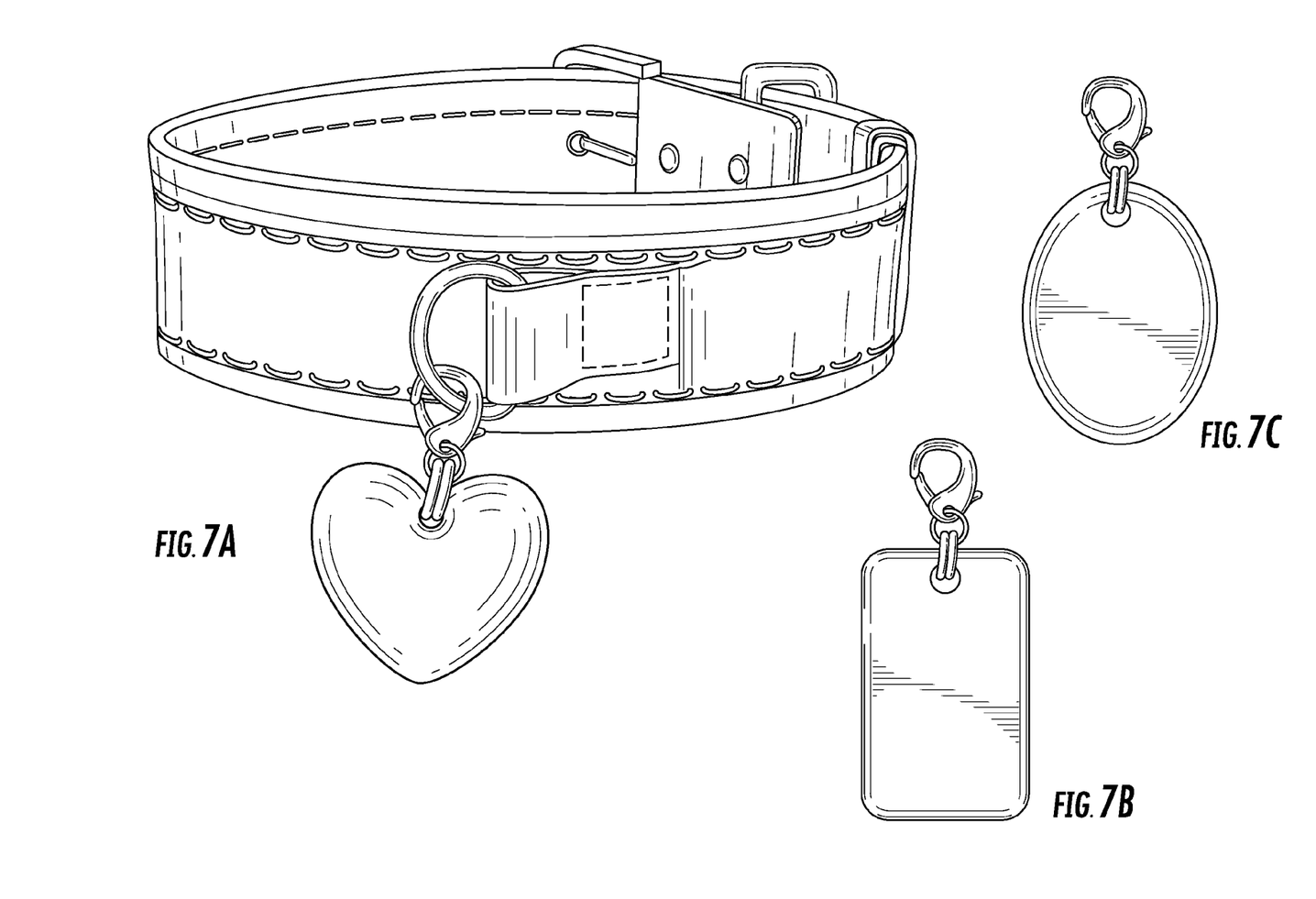
FIGS. 7A-C are schematic diagrams showing how the pendants shown in FIGS. 6A-C can be attached to another article, such as a dog collar.

Replaceable pendants, which can be attached to any support member including a collar, necklace, bracelet, gym bag, purse, etc., can be operably configured as shown in FIGS. 6A-C. As shown, the pendants can be of any shape or size, including the preferred shapes of an oval, a rectangle, or a heart. A clip can be attached to the pendant for securing the pendant to another structure, such as a collar. In this manner, different deodorizing pendants comprising the cellulosic material and deodorizer of the invention can be interchanged on the collar. A mechanism by which such pendants can be secured temporarily to a collar is illustrated in FIG. 7A. Together, the pendants and collar shown in FIGS. 7A-C provide a collar-based deodorizing system for a pet comprising a collar and a plurality of interchangeable pendants formed from a cellulosic plastic with deodorizer impregnated therein and an optional fragrance.

Figure 8A:
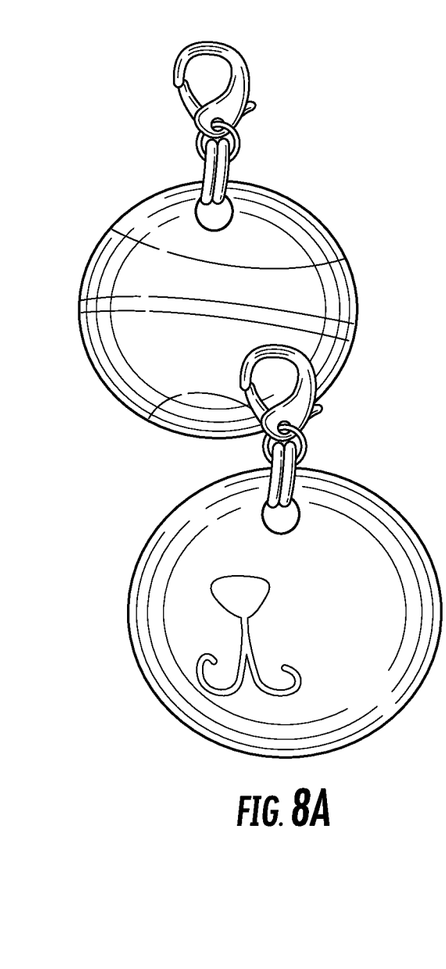
FIGS. 8A-B are schematic diagrams showing various uses of a transparent malodor neutralizer in the form of pendants according to the invention.
Figure 8B:
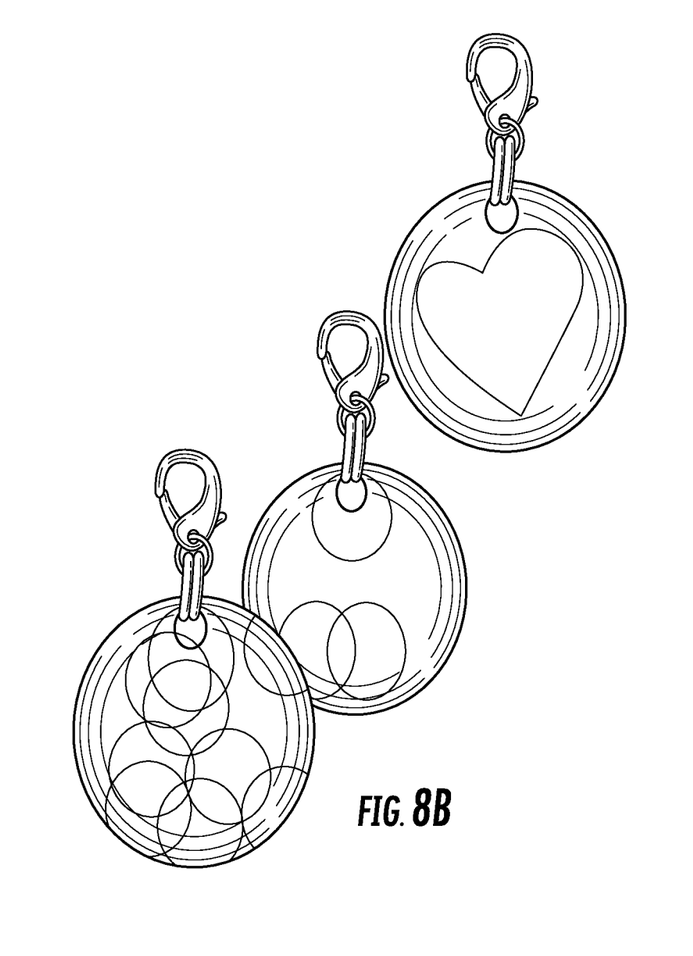

Another embodiment for the pendants of the invention includes those shown in FIGS. 8A and 8B. As shown, a transparent, clear color pendant can be operably configured as a quasi lens for magnifying or otherwise distorting an image placed under the pendant. Indeed, the pendant need not be clear and any color could suffice such that there is sufficient transparency of the material to view the image. The image can be prepared on a waterproof or water resistant paper or plastic and affixed to the underside of the pendant. In this manner, a universal base pendant comprising the cellulosic material and deodorizer and optional fragrance can be prepared, which can then be combined with an unlimited number of designs to impart an appealing aesthetic appearance to the pendant in any desired manner. One mode of manufacturing such pendants is illustrated in the FIGS. 17A-F. More particularly, a plastic sheet (FIG. 17A) can be attached to a pre-formed clear pendant (FIG. 17B) in a manner that provides for magnification of the design imprinted or formed on the plastic sheet (as shown in FIG. 17C). As shown in FIG. 17D, the design on the plastic sheet can be prepared to be attached or adhered to the back side of the cellulose acetate substrate comprising the deodorizing compound and optional fragrance. FIG. 17E provides a front view of the pendant shown in FIG. 17D, while FIG. 17F provides a side view.

Figure 9:
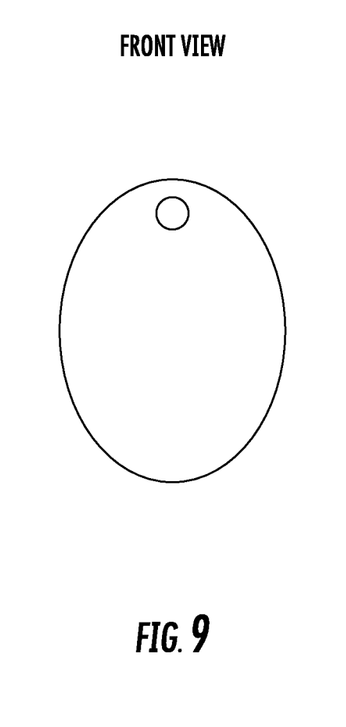
FIG. 9 is a schematic drawing of a pendant of the invention.
Figure 10A:
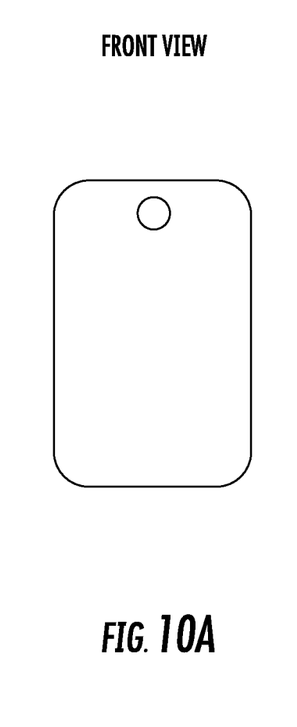
FIGS. 10A-B are schematic drawings of another exemplary pendant according to the invention, respectively showing a top planar view and side elevation view of the pendant.
Figure 10B:
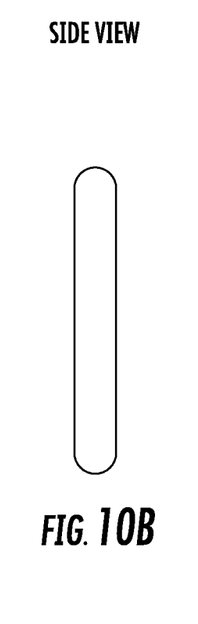

FIGS. 9A, 10A, and 10B provide schematics showing various dimensions that can be used for preparing the cellulosic material (such as cellulose acetate impregnated with a deodorizing compound and optionally a fragrance) in a format acceptable for pendants for dog collars and/or luggage tags.

Figure 11:
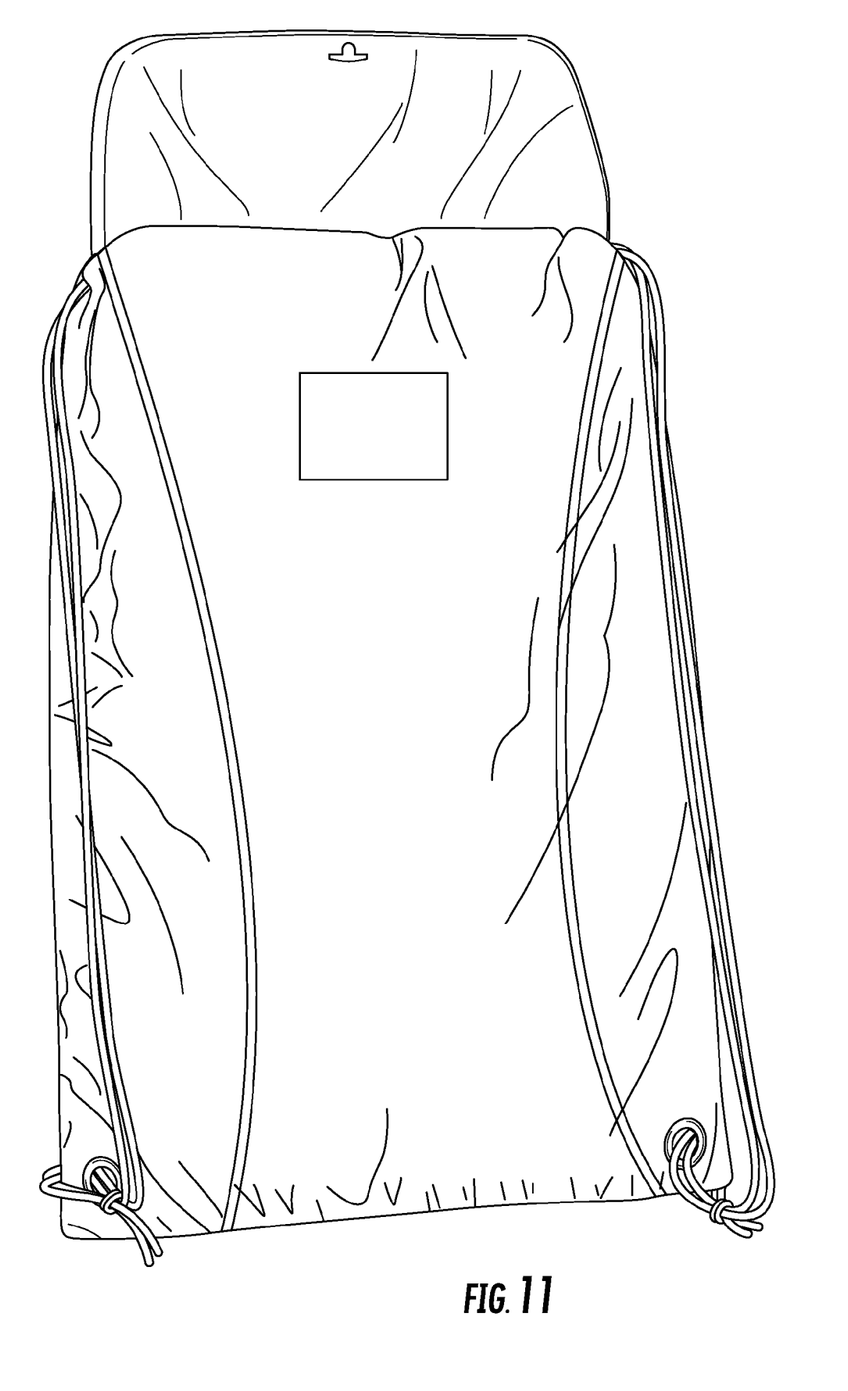
FIG. 11 is a schematic diagram showing a backpack with a pocket for inserting a replaceable disk type malodor neutralizer into the backpack for use in a manner that exposes at least a portion of the disk to the environment outside and/or inside the backpack.
Figure 12A:
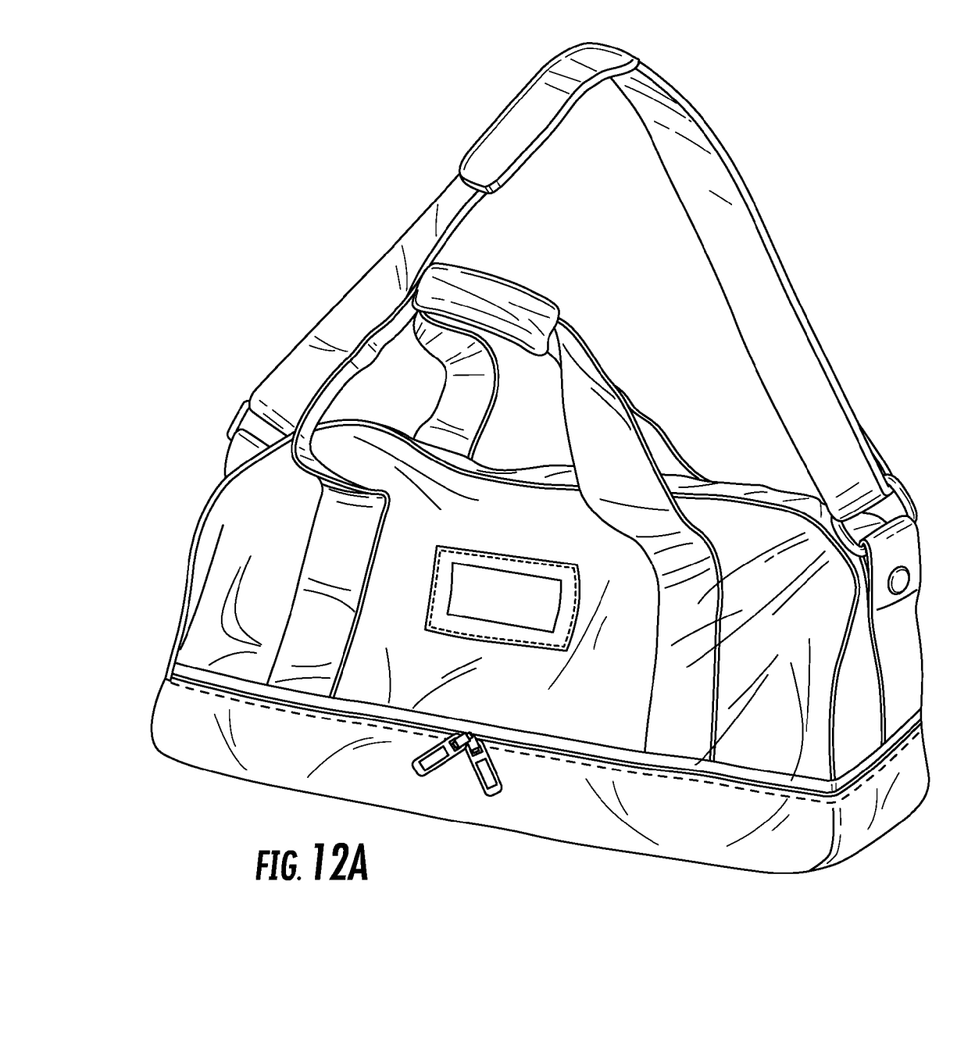
FIGS. 12A-C are schematic diagrams of a gym bag (FIG. 12A) with means (FIG. 12B) for holding a malodor neutralizer disk according to the invention in a manner that exposes the surface of the disk to the interior environment of the gym bag (mesh), and an exemplary package of refill disks (FIG. 12C) for replacing the neutralizers when expired.
Figure 12B:
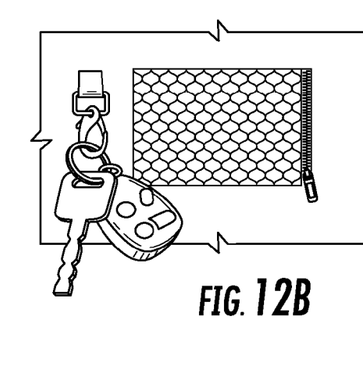
Figure 12C:
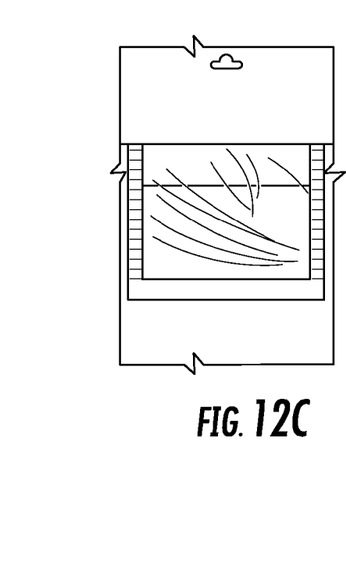

FIGS. 11 and 12A-C provide yet another embodiment for the compositions of the invention. In particular, a substantially planar form of cellulosic material comprising deodorizing agents impregnated therein and optionally a fragrance is prepared as a replaceable insert for bags and purses. A backpack (as shown in FIG. 11) is one vehicle in which such products can be used. A gym bag (FIGS. 12A and 12B) is another appropriate use. As shown, the bags can be operably configured to have disposed therein a pocket. The pocket is preferably transparent to the outside of the bag and the interior of the bag is not accessible through the exterior of the pocket. As such the removable insert comprising the plastic infused deodorizing composition can be manufactured for example to have the brand name of the product, brand name of the bag, team sports name, or person's name imprinted thereon or otherwise made visible, such as by the procedure exemplified in FIGS. 8 and 15. The pocket on the interior side of the bag is comprised of mesh or other breathable material to allow for the active ingredients of the insert to interact with and prevent, treat, or otherwise neutralize any malodors present and to allow for any perfumes impregnated in the product to be dispersed into the bag. The pocket preferably comprises means for releasably retaining the insert within the pocket until it is desired to replace it. As shown in FIG. 12C, replacement cartridges or inserts can be packaged for sale.

Figures 13, 14:
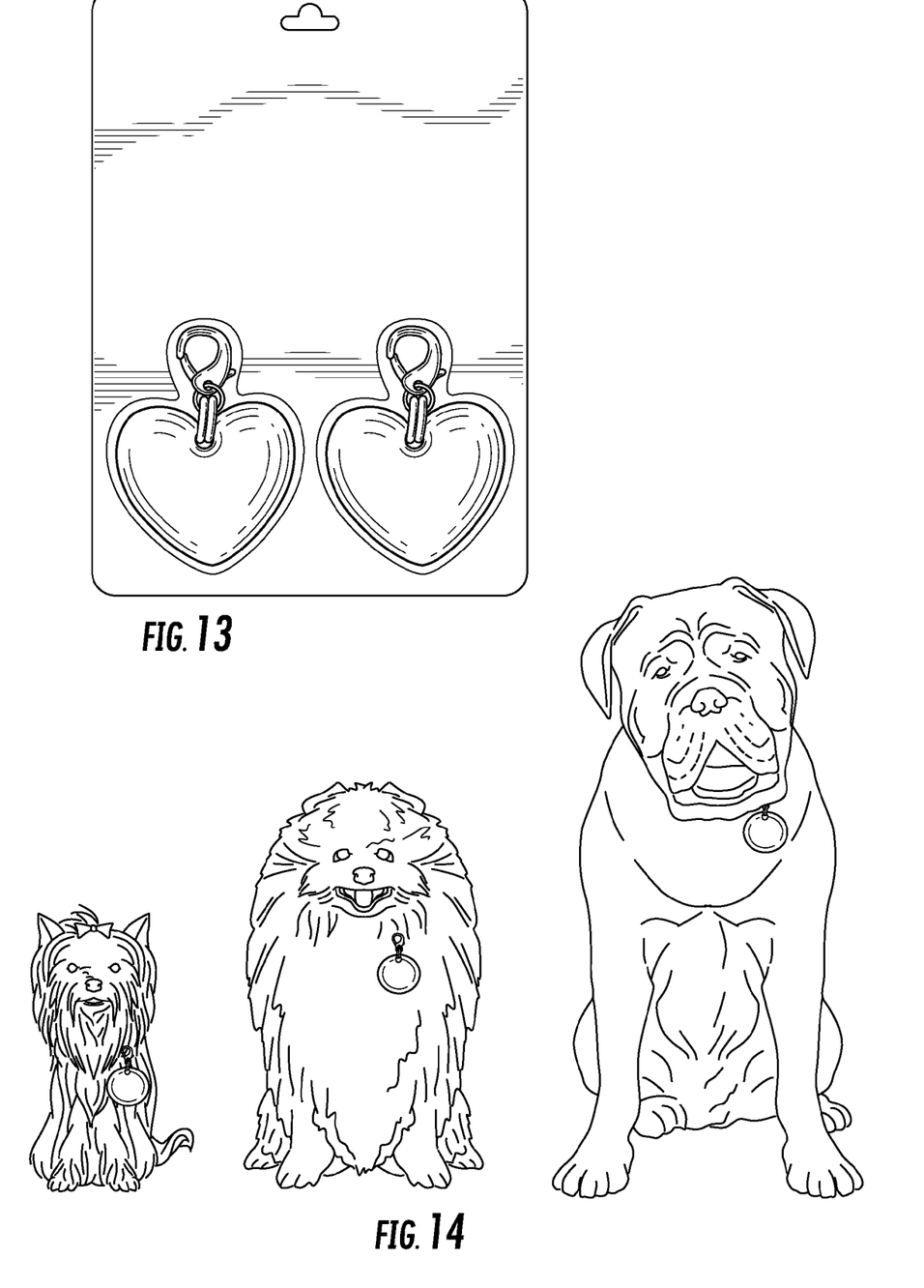
FIG. 13 is a schematic diagram of an exemplary package of refill malodor neutralizer pendants according to embodiments of the invention.
FIG. 14 is a schematic diagram showing use of various malodor neutralizer pendants according to the invention on dogs.
Figure 15A:
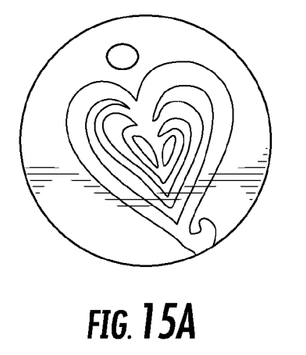
FIGS. 15A-F are photos of a transparent malodor neutralizer substrate according to embodiments of the invention where a design (FIG. 15A) can be disposed below the transparent substrate (FIG. 15B) to provide a pendant (FIG. 15C) of the invention, and one method for preparing such pendants is illustrated in FIGS. 15D-F.
Figure 15B:
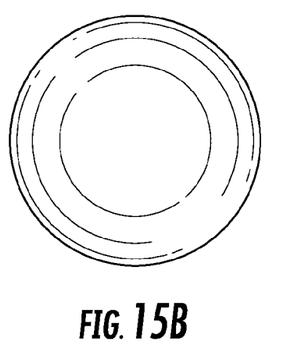
Figure 15C:
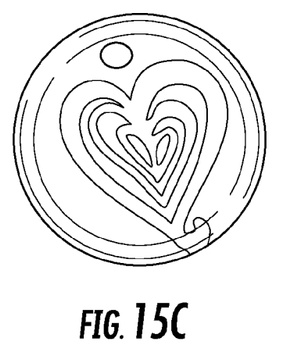
Figure 15D:
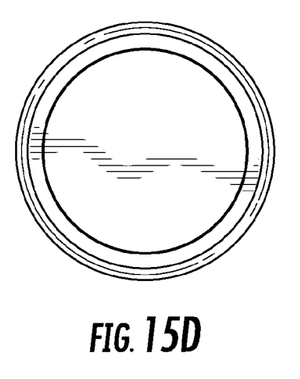
Figure 15E:
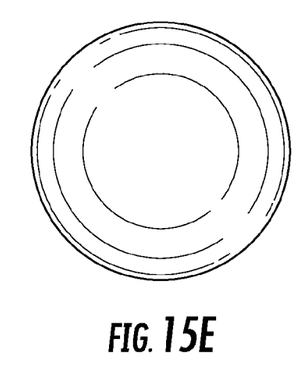
Figure 15F:
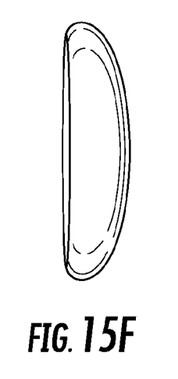

As shown in FIGS. 13 and 14, a month's supply of pendants (eg, two pendants) can be packaged for sale (typically, at the concentrations recommended in this application, the longevity of the product is effective for about 2-3 weeks). Various configurations and designs of the pendants are also provided. Of particular note is the glass-type appearance of the pendants manufactured according to embodiments of the invention, which are transparent even when including the impregnated deodorizer and optional perfume.

Figure 16:
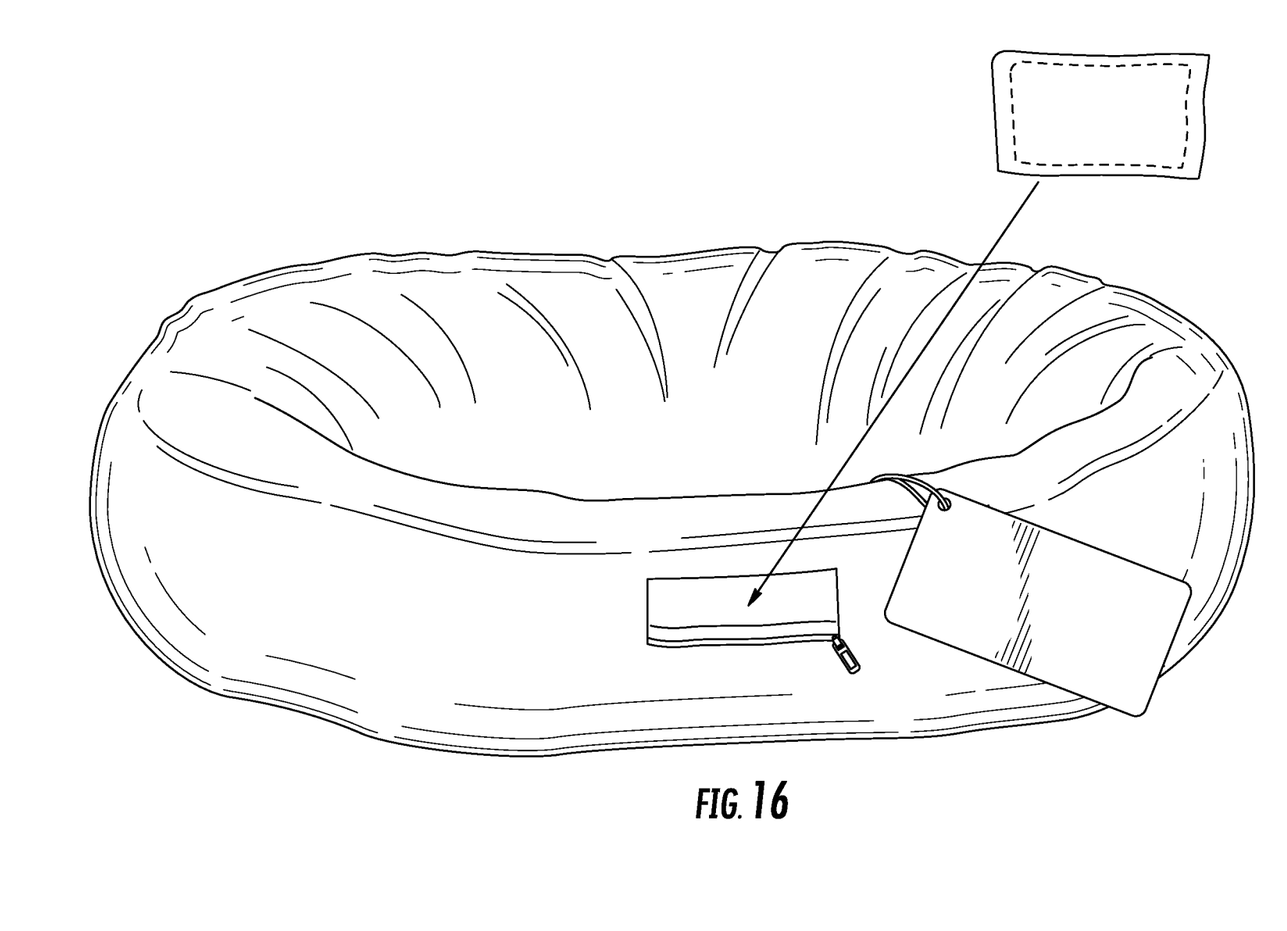
FIG. 16 is a schematic diagram showing a pet bed with a pocket for inserting a replaceable sachet comprising the malodor neutralizer of the invention into the pet bed.

FIG. 16 provides yet another example of the possible applications available from embodiments of the present invention. As shown in FIG. 16, the malodor neutralizer and optional fragrance can be in the form of a sachet that is used in conjunction with a pet bed. Alternatively, the sachets can be used alone in drawers or added to purses or gym bags but can also be configured to be inserted into other articles, such as pendants, which can be worn as necklaces or attached to articles of clothing or other personal items. The pellets can be prepared from the cellulosic materials comprising the deodorant and optional fragrance by forming solutions of the premelt type materials with the active ingredients, then molding or casting into pellets. As pellets, there is an increased surface area for the active deodorizing ingredients to be dispersed. Preferably, the sachets enveloping the pellets comprise a breathable material to allow for aromatic malodors to interact with the active malodor neutralizing agents, as well as to allow the perfumes, if used, to escape into the atmosphere.

In preferred embodiments, the sachet can comprise the malodor and fragrance in the form of pellets secured within a pillow type sachet. The sachet can then be inserted into a zippered pocket of the pet bed for use. Once the malodor neutralizer and/or fragrance has lost its function, the sachet can be replaced with another similar sachet. According to this embodiment, the product can provide for an odor free or reduced odor environment where a pet sleeps or rests, making the pet bed a more desirable addition to the human household.

The products of the invention can also be extended for use in litter boxes to reduce or eliminate unwanted odors caused by pet waste. The malodor neutralizer can be in any form convenient for this purpose, but is preferably incorporated into an inconspicuous part of the cat box. For example, the product can be disposed on the lid of the cat box to prevent odors from emanating away from the cat box into living areas of a human household.

The deodorizing compounds, methods, and delivery systems of embodiments of the present invention are applicable to a wide variety of uses. One of ordinary skill in the art will know how to modify embodiments of the invention disclosed in this specification to achieve numerous types of applications. Embodiments of the invention include deodorant devices and odor controlling and/or reducing devices. Embodiments of the invention can be used to treat a variety of articles and situations, including for example pets, pet beds, litter boxes and other items associated with pets, pet odors, or pet waste; purses, gym bags, luggage; pig pens, chicken coops, cow barn enclosures, horse barn enclosures, kennels, veterinary facilities, cattle cars, and zoo animal pens to name a few. A common object of embodiments of the invention is to treat, reduce, or eliminate continuously prevailing odors which are potentially offensive to the human and/or animal sense of smell, eg, malodors.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. It is intended that the specification and examples be considered as exemplary in nature and that variations that do not depart from the essence of the invention are to be within the scope of the invention.

Therefore, embodiments of the present invention are well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While embodiments are described in terms of "comprising," "containing," or "including" various components or steps, embodiments can also "consist essentially of" or "consist of" the various components and steps. Further, all numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined in this specification. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A solid plastic biodegradable deodorizer composition comprising:
   a solid plastic cellulose acetate based substrate comprising cellulose acetate in an amount ranging from about 30-70% by weight of the substrate and having at least 96% biodegradability;
   a plasticizer present in the solid plastic cellulose acetate based substrate in an amount ranging from about 10-50% by weight of the substrate; and
   solubilized zinc ricinoleate impregnated into the solid plastic cellulose acetate based substrate in an amount ranging from about 0.01% to about 3.0% by weight of the substrate;
   wherein the solid plastic cellulose acetate based substrate is in the form of a pendant operably configured to hang from a pet collar, or an elongated strip for incorporation into a pet collar, or an elongated strip comprising a through hole at each of opposing ends of the strip to allow for opposing ends of a pet collar to be received and secured therethrough, or a plurality of pellets or beads contained in a sachet configured to be received by a breathable pocket of a bag or pet bed, or an elongated planar member capable of insertion into a breathable pocket on an interior of a bag.

2. The deodorizer composition of claim 1, further comprising a fragrance impregnated into the substrate that does not contain nitrogen or sulfur.

3. The deodorizer composition of claim 1, wherein the solid plastic cellulose acetate based substrate is in the form of a pendant operably configured to hang from a pet collar.

4. A malodor neutralizer dog tag comprising:
   a solid plastic cellulose acetate based substrate comprising cellulose acetate in an amount ranging from about 30-70% by weight of the substrate and having at least 96% biodegradability;
   solubilized zinc ricinoleate impregnated into the solid plastic cellulose acetate based substrate in an amount ranging from about 0.01% to about 3.0% by weight of the substrate; and
   a fragrance impregnated into the solid plastic cellulose acetate based substrate that does not contain nitrogen or sulfur.

5. The dog tag of claim 4, wherein the solid plastic cellulose acetate based substrate is a solid composition comprising a plasticizer in the range of about 10-30% by weight of the composition.

6. The dog tag of claim 4, wherein the solid plastic cellulose acetate based substrate is a solid composition comprising a plasticizer in the range of about 30-50% by weight of the composition.

* * * * *